US009149553B2

(12) United States Patent
Akitsu et al.

(10) Patent No.: US 9,149,553 B2
(45) Date of Patent: *Oct. 6, 2015

(54) LIQUID SPRAYER (71) Applicants: Hiromi Akitsu, Yamashina Ku (JP);
Shiang Aling Shiu Shu, Taipei (TW);
Christian Dinner, Préverenges (CH);
Jerry Ping Hsin Chu, Taipei (TW)

(72) Inventors: Hiromi Akitsu, Yamashina Ku (JP);
Shiang Aling Shiu Shu, Taipei (TW);
Christian Dinner, Préverenges (CH);
Jerry Ping Hsin Chu, Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 14/319,949

(22) Filed: Jun. 30, 2014

(65) Prior Publication Data
US 2015/0014435 A1 Jan. 15, 2015

Related U.S. Application Data (63) Continuation-in-part of application No. 13/619,831, filed on Sep. 14, 2012, now Pat. No. 9,016,595.

(30) Foreign Application Priority Data

May 7, 2012 (JP) .................................. 2012-106349

(51) Int. Cl.
B05B 17/06 (2006.01)
B05B 17/00 (2006.01)
B05B 15/06 (2006.01)
B05B 15/00 (2006.01)
A61L 9/14 (2006.01)

(52) U.S. Cl.
CPC .................. *A61L 9/14* (2013.01); *B05B 15/005* (2013.01); *B05B 15/065* (2013.01); *B05B 17/0646* (2013.01); *B05B 17/0661* (2013.01); *B05B 17/0684* (2013.01)

(58) Field of Classification Search
CPC ...... B05B 15/005; B05B 15/065; B05B 17/0646; B05B 17/0684; A61L 9/14; A61L 2209/132
See application file for complete search history.

(56) References Cited

U.S. PATENT DOCUMENTS

| 4,301,093 | A  | * | 11/1981 | Eck ................................... 261/1 |
| 6,550,472 | B2 | * | 4/2003 | Litherland et al. ........ 128/200.18 |
| 2007/0235555 | A1 | * | 10/2007 | Helf et al. .................. 239/102.2 |
| 2008/0011875 | A1 | * | 1/2008 | Sipinski et al. ............. 239/102.2 |
| 2009/0065600 | A1 | * | 3/2009 | Tranchant et al. ................ 239/4 |

(Continued)

FOREIGN PATENT DOCUMENTS

| JP | 2007203225 A | 8/2007 |
| JP | 2007203226 A | 8/2007 |

(Continued)

*Primary Examiner* — Darren W Gorman
(74) *Attorney, Agent, or Firm* — Laura M. Lloyd; Leech Tishman Fuscaldo & Lampl (57) ABSTRACT A transducer type liquid sprayer in that mist can be dispersed widely even when the liquid sprayer is dispersed in a relatively low position. The liquid sprayer contains a storage tank for storing spray liquid that can be easily replaced together with a core for soaking up the spray liquid from the storage tank. The liquid sprayer includes a spray liquid storage unit and a main body for supporting the spray liquid storage unit and a power supply unit. A spray hole is formed in the lid member and a transducer is also disposed inside the lid member and electrically connected to the power supply unit. The transducer is in contact with a front side of a tip end portion of the core with the front face of the transducer oriented forward and upward.

19 Claims, 8 Drawing Sheets (56) References Cited

U.S. PATENT DOCUMENTS

2009/0114737 A1* 5/2009 Yu et al. .................. 239/69
2011/0011948 A1* 1/2011 Huang .................... 239/44

FOREIGN PATENT DOCUMENTS

| JP | 2010007899 A | 1/2010 |
|---|---|---|
| JP | 2010119562 A | 6/2010 |
| WO | 00/51747 A1 | 9/2000 |
| WO | 02/09888 A1 | 2/2002 |
| WO | 03/066115 A2 | 8/2003 |
| WO | 03/099458 A2 | 12/2003 |
| WO | 2004/043502 A1 | 5/2004 |
| WO | 2004/048002 A1 | 6/2004 |
| WO | 2004/056492 A1 | 7/2004 |
| WO | 2006/004891 A1 | 1/2006 |
| WO | 2006/004902 A1 | 1/2006 |
| WO | 2006/110794 A1 | 10/2006 |
| WO | 2008/103238 A1 | 8/2008 |
| WO | 2010/021716 A1 | 2/2010 |

* cited by examiner

LIQUID SPRAYER

CROSS-REFERENCE TO RELATED APPLICATIONS

The instant patent application is a continuation-in-part of U.S. non-provisional patent application Ser. No. 13/619,831, filed Sep. 14, 2012, that claims priority to Japanese Patent Application No. 2012-106349, filed May 7, 2012, both applications are hereby incorporated by reference in its entirety for all purposes.

FIELD OF THE INVENTION

The present invention relates to a liquid sprayer, more specifically to a transducer type liquid sprayer.

BACKGROUND

As is known in the art, there are conventional spray cans using propellants as liquid sprayers for spraying liquid fragrance or the like. These spray can type liquid sprayers have safety issues because of the use of flammable gas as a propellant. Therefore, in recent years, transducer type liquid sprayers for spraying liquid fragrance have been developed that use transducers for generating ultrasonic vibration.

Liquid sprayers using a transducer, such as disclosed in Japanese Patent No. JP 2010-7899, include a liquid storage tank for storing spray liquid, a mist producing means for turning the spray liquid into mist, and a spray liquid supply means for supplying the spray liquid in the liquid storage tank to the mist producing means. The spray liquid supply means includes a first liquid retaining body having one end disposed at a predetermined position in the liquid storage tank to absorb the spray liquid in the liquid storage tank, a substantially cylindrical second liquid retaining body brought into contact with the other end of the first liquid retaining body and having a predetermined inside diameter and a predetermined outside diameter, and a third liquid retaining body having one end brought into contact with an outer peripheral face of the second liquid retaining body at a predetermined contact pressure and the other end brought into contact with the mist producing means at a predetermined contact pressure.

However, the claimed liquid storage tank for storing the spray liquid is detached from the liquid retaining body for absorbing the spray liquid in the liquid storage tank and only the liquid storage tank is attached and detached to add the spray liquid. Therefore, if the sprayer is used for a long term, solid components and impurities included in the spray liquid accumulate in the liquid retaining body and the liquid retaining body cannot soak up the spray liquid.

Moreover, the liquid retaining body is housed in an L-shaped casing making it difficult to detach and replace the liquid retaining body.

Further, at least some prior art liquid sprayers have the spray liquid and spray hole positioned such that the spray mist is sprayed in an upward vertical direction, precluding wall mounting high on the wall, as the spray mist will be sprayed onto the ceiling. Furthermore, in these types of sprayers, if they are placed lower to the ground, the mist can become an eye or nasal irritant if it is dissipated in close proximity to someone nearby.

Therefore, there is a need for transducer type liquid sprayers that can be positioned high on a wall as well as be able to easily replace the liquid storage cartridge.

SUMMARY

The objectives of the invention are to achieve a transducer type liquid sprayer where a storage tank for storing spray liquid can be easily replaced together with a core for soaking up the spray liquid from the storage tank. In addition, the liquid sprayer has a horizontally directed spray mist, such that the sprayer may be mounted higher on a wall.

In order to realize these objectives, the present inventor repeatedly carried out test production and experiments to achieve the invention described herein. As a result, the inventor has found a notable fact that a transducer may be mounted on a front facing lid, and when the lid and transducer are detached from the core, a spray liquid storage unit can be easily attached and detached. The transducer is in contact with a front side of a tip end portion of a core; the front face of the transducer is oriented forward and upward. As a result, a spray hole is positioned on the main body facing the front face of the transducer even when the liquid sprayer is disposed in a relatively low position.

According to the present invention, a liquid sprayer for dispensing a spray liquid is provided that achieves the above described objectives. The liquid sprayer comprises a main body having a support member having a back face, an upper portion, and a lower portion, and a power supply unit positioned in the interior of the support member, on the upper portion of the support member. A lid member having a front face is rotatably connected to the support member. When the lid member is positioned in an open position, the upper portion and lower portion of the support member are revealed. When the lid member is positioned in the closed position, the lid member closes down on the support member, forming the main body. The lid member also has a spray hole formed on the front face of the lid member. A spray liquid storage unit is supported by and positioned on the lower portion of the support member, the spray liquid storage unit has a spray liquid housed in a storage tank and a core for soaking up spray liquid. The spray liquid storage unit is removable from the main body when the lid member is in the open position. A transducer is disposed inside the lid member and electrically connected to the power supply unit, such that when the lid member is in the closed position, the transducer is in contact with and pressed against the front side of the tip end portion of the core that is protruding from the storage tank of the spray liquid storage. The front face of the transducer is oriented upward and forward. The tip end portion of the core extends in a vertical direction forming an inclination angle of 10° to 45° between the front face of the tip end portion of the core and the front face of the transducer. The core, transducer, and spray hole are substantially aligned, such that when electric power is supplied from the power supply unit to the transducer, the spray liquid retained in the core is turned into a spray mist by vibration of the transducer and sprayed outside the main body through the spray hole.

Preferably, when the lid member is in an open position, the upper portion and lower portion of the support member are revealed, and when the lid member is in a closed position, the transducer is disposed parallel to a front face of the core. In this position, the core, transducer and spray hole will be substantially aligned to dispense the spray liquid in a spray mist upon the application of power to the transducer.

In other embodiments, the lid member has side faces rising from opposite sides of the front face of the lid member such that the lid and support member form a shell that makes up the main body. More preferably, a support arm is positioned between opposite side faces of the lid member and the transducer is affixed to the support arm that raises and lowers the transducer with the lid member and aligns the transducer with the spray hole and core. The liquid sprayer may also have one or more support members for supporting one or both of the power supply unit and the spray liquid storage unit.

According to a preferred embodiment, the spray hole is formed in the lid member so as to face a front face of the core when the lid member is closed onto the support member. The transducer faces the spray hole and is disposed inside the lid member. The transducer is in close contact with and pressed against the front face of the core and is supported by the support member when the lid member is closed onto the support member. Therefore, the transducer is detached from the core when the lid member is opened and the spray liquid storage unit supported on the support member can be easily attached and detached. Due to the orientation, forward and upward of the transducer in contact with the front side of the tip end portion of the core facing the spray hole, the spray liquid mist spouts forward and upward and can be dispersed widely. Moreover, because the transducer is in contact with the edge portion of the front side of the tip end portion of the core, the contact area between the transducer and the core can be small. As a result of the small contact area, only a small amount of spray liquid is lost and not turned into mist and evaporation is prevented when the operation of spraying is ceased extending the life of the spray storage tank.

BRIEF DESCRIPTION OF THE DRAWINGS

These and other features, aspects and advantages of the present invention will become better understood with regard to the following description, appended claims, and accompanying figures where:

FIG. 1 is a perspective view showing an outward appearance of a liquid sprayer according to one embodiment of the invention;

FIG. 2 is a front view of an inside of a lid member of the liquid sprayer shown in FIG. 1;

FIG. 3 is a sectional view showing a section of the lid member shown in FIG. 2 and taken along line A-A;

FIG. 4 is a front view showing an inside of a support member of the liquid sprayer shown in FIG. 1;

FIG. 5 is a sectional view showing a central vertical sectional view of the liquid sprayer shown FIG. 1;

FIGS. 6A, 6B, and 6C are explanatory sectional views showing open and closed states of the lid member and the support member of the liquid sprayer shown in FIG. 1;

FIG. 7 is an end view of a core and a transducer shown in FIG. 6A cut in a horizontal direction in a position where they are in contact with each other; and FIGS. 8A and 8B are explanatory views showing a positional relationship between the core and the transducer according to another embodiment of the invention.

DETAILED DESCRIPTION

Various embodiments provide a transducer type liquid sprayer that can be mounted high on wall, easily replace liquid storage canisters, and minimize spray liquid loss and evaporation extending the life of the liquid storage canisters. The liquid sprayer and method of assembling the liquid sprayer will now be disclosed in detail.

All dimensions specified in this disclosure are by way of example only and are not intended to be limiting. Further, the proportions shown in these Figures are not necessarily to scale. As will be understood by those with skill in the art with reference to this disclosure, the actual dimensions and proportions of any system, any device or part of a system or device disclosed in this disclosure will be determined by its intended use.

Methods and devices that implement the embodiments of the various features of the invention will now be described with reference to the drawings. The drawings and the associated descriptions are provided to illustrate embodiments of the invention and not to limit the scope of the invention. Reference in the specification to “one embodiment” or “an embodiment” is intended to indicate that a particular feature, structure, or characteristic described in connection with the embodiment is included in at least an embodiment of the invention. The appearances of the phrase “in one embodiment” or “an embodiment” in various places in the specification are not necessarily all referring to the same embodiment.

Throughout the drawings, reference numbers are re-used to indicate correspondence between referenced elements. In addition, the first digit of each reference number indicates the figure where the element first appears.

As used in this disclosure, except where the context requires otherwise, the term “comprise” and variations of the term, such as “comprising”, “comprises” and “comprised” are not intended to exclude other additives, components, integers or steps.

In the following description, specific details are given to provide a thorough understanding of the embodiments. However, it will be understood by one of ordinary skill in the art that the embodiments may be practiced without these specific detail. Well-known circuits, structures and techniques may not be shown in detail in order not to obscure the embodiments. For example, circuits or structure may be shown in block diagrams in order not to obscure the embodiments in unnecessary detail.

Referring now to FIG. 1, there is shown a liquid sprayer 1 according to one embodiment of the invention. As can be seen, the liquid sprayer 1 comprises a case main body 4 (main body) having a lid member 2 that forms a front face side and a support member 3 forming a back face side of the main body. A spray hole 8 is for discharging the spray liquid that has been turned into the mist. The spray hole 8 of the lid member 2 opens in a portion of the lid member 2 Preferably, the spray hole 8 is positioned closer to the upper portion of the front face, but in other embodiments, the spray hole 8 is centrally located. In some embodiments, the back face of the support member may have impressions or grooves for wall mounting.

Referring now to FIG. 2, there is shown a front view of an inside of the lid member 2 of the liquid sprayer 1, and a sectional view of the lid member 2 taken along line A-A. As can be seen, the case main body 4 houses spray liquid storage unit 5, that stores spray liquid, a transducer unit 6, and a power supply unit 7. The transducer unit 6 turns the spray liquid stored in the spray liquid storage unit 5 into mist, and the power supply unit 7 supplies electric power to the transducer unit 6. The lid member 2 is formed by left and right side faces 10 and 11 and upper and lower faces 12 and 13. In one embodiment, the upper and lower faces 12 and 13 extend backward in a rising manner from a front face 9 at a substantially central portion thereof. The spray hole 8 for discharging the spray liquid that has been turned into the mist by the transducer unit 6 is positioned between the left and right side faces 10 and 11. An optional pair of lock holes 19 are positioned in the lower face 13. In some embodiments, the back face of the support member may have impressions or grooves for wall mounting.

In another embodiment (not shown), the main body of the liquid sprayer comprises a power indicator display electrically connected to the power supply unit 7 for indicating to a user if additional power is needed to supply the unit (e.g., batteries). In another embodiment (not shown) the main body of the liquid sprayer comprises a light sensor, motion detector, or other means for automatic turn off or turn on of the device.

In one embodiment, one or more fitting shafts 14 are positioned on the inner sides of the left and right side faces 10 and 11. The fitting shafts 14 are connected to the support member 3, and protrude to face each other from back upper end portions and support plates 15*a* and 15*b*. The support plates 15*a* and 15*b* support the transducer unit 6 and are positioned to face each other at positions above the spray hole 8.

Figure 1:
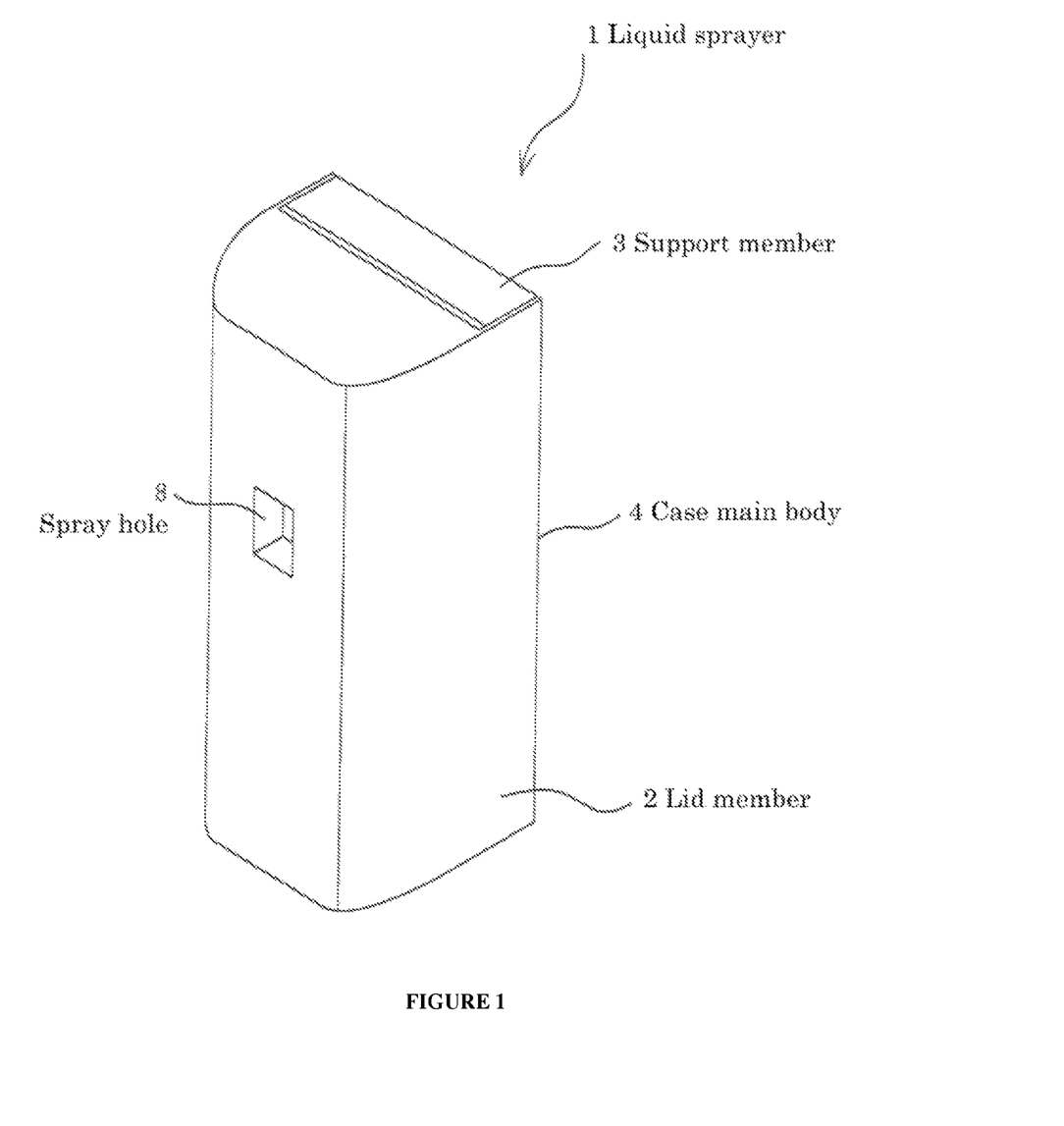
Figure 2:
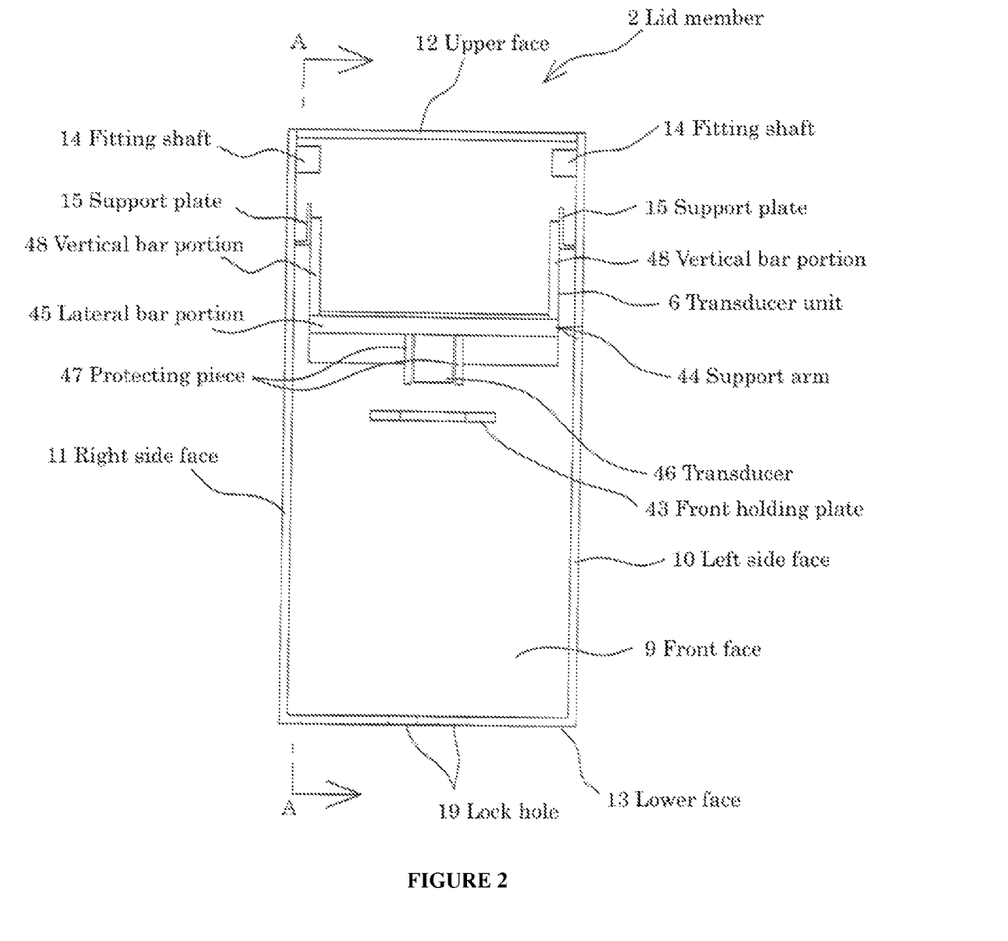
Figure 3:
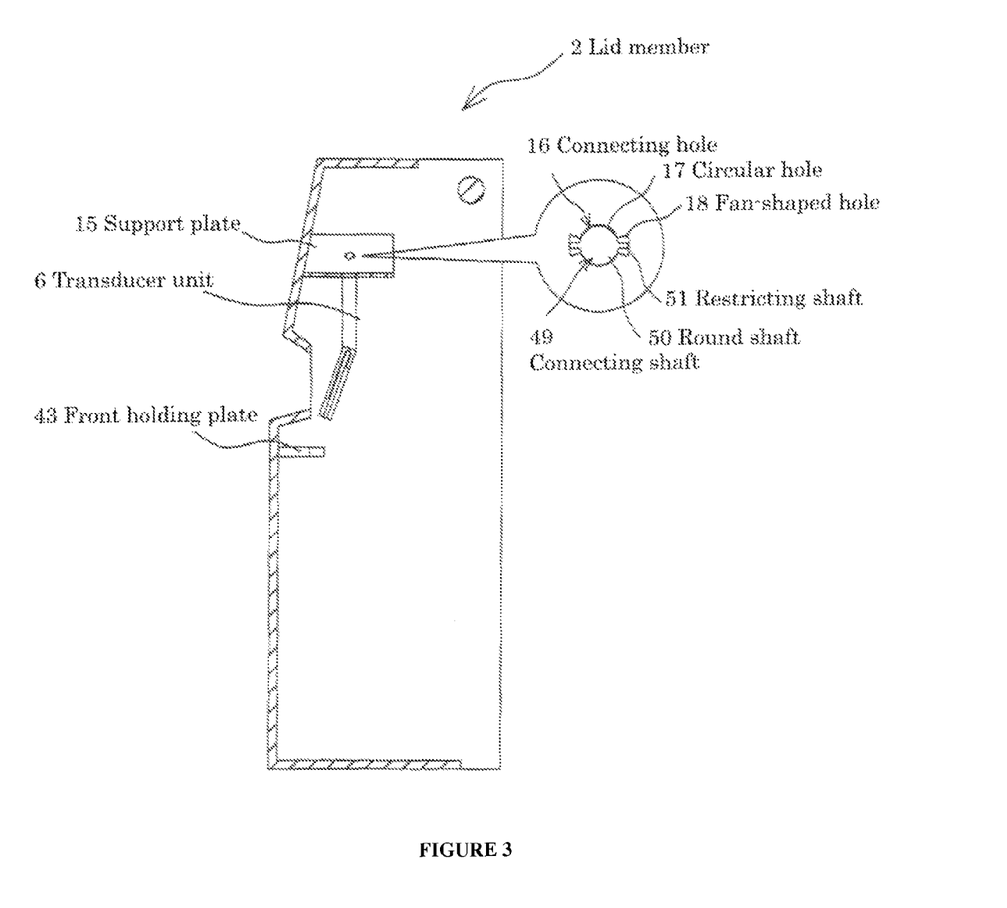
Figure 4:
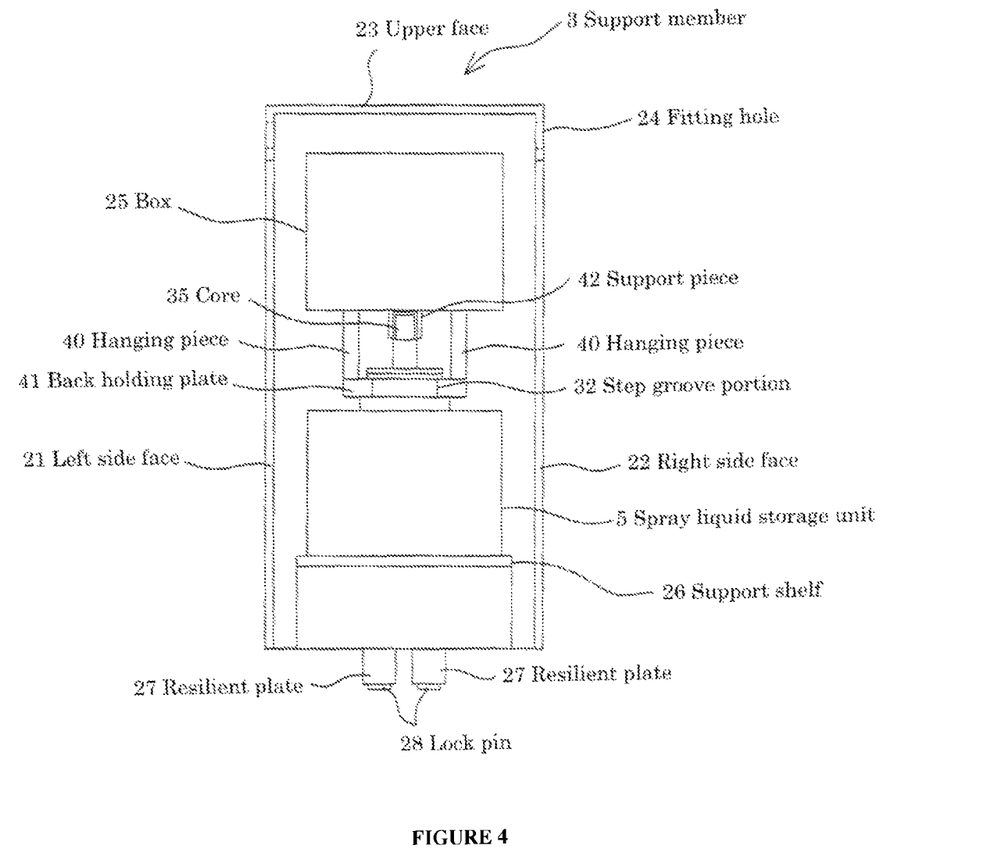

Referring again to FIG. 2, the transducer unit 6 may include a support arm 44 having a recessed shape. A transducer 46 may be fixed to a lateral bar portion 45 of the support arm 44, and vertical bar portions 48*a* and 48*b*. The support arm 44 extends between vertical bar portions 48*a* and 48*b*, while tilting, from the lateral bar portion 45. The lateral bar portion 45 is provided with two protecting pieces 47*a* and 47*b*. The protecting pieces 47*a* and 47*b* are positioned parallel on opposite sides of the transducer 46.

The transducer 46 is preferably a metal plate having a mesh interior that is mounted to a ceramic plate that is electrically connected to the power supply unit. Preferably, the metal plate is a rectangular plate of 7 mm in length and 8 mm in width and comprised of a Ni—Co alloy. Preferably the transducer 46 is resistant to corrosion from the spray liquid. The interior of the metal plate is comprised of a mesh material that forms the spray mist when vibrated in contact with the core and spray liquid. Preferably, the mesh size is less than 50 μm, with a hole size of less than 5 μm, with total holes on the metal plate of less than 1200 holes. However, the dimension (size) and holes are determined according to the power consumption. The metal plate is mounted on a side to a ceramic plate and electrically connected to the power supply to vibrate the transducer 44. The ceramic plate is preferably 6 mm in length and 10 mm in width.

Referring now to FIG. 3, a sectional view of a section of the lid member 2 shown in FIG. 2, taken along line A-A is shown. Also shown in FIG. 3 is an expanded view of the support plates 15*a* and 15*b*. Positioned on each of the support plates, 15*a* and 15*b*, are a connecting shaft 49 and a restricting shaft 51, as well as a connecting hole 16 that is formed by a circular hole 17 and a pair of fan-shaped holes 18. Fan-shaped holes 18 extend from the circular hole 17 to be symmetric with respect to a point from the circular hole 17 (see an enlarged view of the connecting hole 16 shown in FIG. 3). The connecting shafts 49 protrude outward at the tip ends of each of the vertical bar portions 48*a* and 48*b* of the support arm 44 (shown previously in FIG. 2). Each of the connecting shafts 49 includes a round shaft 50 and restricting shafts 51. Restricting shafts 51 extend symmetrically with respect to a point from the round shaft 50 (see the enlarged view of the connecting shaft shown in FIG. 3).

Now referring back to FIG. 2, by fitting the opposite connecting shafts 49 into the connecting holes 16 in the support plates 15, the support arm 44 can turn between the opposite support plates 15*a* and 15*b* of the lid member 2. Turning of the support arm 44 is restricted by interference between the restricting shafts 51 of the connecting shafts 49 and the fan-shaped holes 18 of the connecting holes 16.

As shown in FIG. 4, the support member 3 is formed by left and right side faces 21 and 22 and an upper face 23 extending forward in rising manners from a back face 20 disposed to be sandwiched between the opposite side faces of the lid member 2. The upper face 12 of the lid member 2 and the upper face 23 of the support member 3 form an upper face of the case main body 4. The fitting shafts 14 of the lid member 2 (previously shown in FIG. 2) insert into fitting holes 24. The fitting holes 24 are placed in the upper end portions of the left and right side faces 21 and 22. Therefore, the fitting shafts inserted into the fitting holes 24 act as rotary shafts so the lid member 2, connected to support member 3, can turn.

As shown in FIG. 4, the power supply unit 7 includes the box 25 for housing a battery and a control board. A lower face of the box 25 is provided with a back holding plate 41 supported by a pair of hanging pieces 40. Extending downward from box 25 are the following: the pair of hanging pieces 40, support pieces 42 in between the paired hanging pieces 40. A back holding plate 41 is formed in a U shape in order to fit in the step groove portion 32 of the storage tank 29 disposed on the support shelf 26. In embodiments where the step groove portion 32 is fitted in the back holding plate 41, a back side of the inner tube portion 34 protruding from the opening portion 31 is supported by the support pieces 42. In those embodiments, in the interior of the lid member 2, a front holding plate 43 protrudes outward and is positioned to face the back holding plate 41. In some embodiments, the box 25 may contain a key pad for setting automatic spray intervals. The key pad may be a buttons or an electronic display, such as an LED display with programmable settings, such as from 1 to 5 second intervals, preferably 2 second intervals every 15 or 30 minutes, etc., or a manual setting, as may be desired by the user.

As power-supply voltage of the power supply unit 7, DC 4.5 V, 6.0 V, and 7.5 V may be used, by way of example. It is also possible that magnitude of the voltage can be changed. As power for the power supply unit 7, AC supplied from a battery or a wall outlet may be converted into DC by an AC to DC converter. Both the battery and the converter may be mounted so as to switch between the power from the battery and the power from the wall outlet.

Referring to FIG. 5, inside the back face 20 of support member 3, a box 25 housing the power supply unit 7 is fixed to an upper portion of the support member 3. The spray liquid storage unit 5 is disposed at a lower portion of the back face of support member 3 fixed to support shelf 26. As shown in FIG. 5, at a lower end portion in the support member 3, resilient plates 27, having U shapes in a side view, protrude forward with only their upper ends fixed to the back face 20 and lock pins 28. The lock pins 28 protrude downward from the resilient plates 27 and can move in a vertical direction as the resilient plates 27 bend. In this way, when the lid member 2 is closed onto the support member 3, the lock pins 28 of the support member 3 are fitted into the lock holes 19, 19 into the lid member 2 to lock opening and closing of the lid member 2 with respect to the support member 3. In one embodiment a support shelf 26 is movable in the vertical direction with respect to the inside of the back face 20 of the support member 3. In another embodiment the support shelf 26 may be removed and replaced. Therefore, spray liquid storage units 5 of different sizes may be used.

Referring again to FIG. 5, the spray liquid storage unit 5 is formed by a storage tank 29 that stores the spray liquid and a core 35 for soaking up the spray liquid from the storage tank 29. The storage tank may be made from suitable materials for holding spray liquids such as polymers and glass. Preferred materials are recyclable.

In another embodiment, the storage tank 29 has an opening portion 31, comprising a liquid soaking holder 30 is inserted in the upper face 12. An outer side face of the opening portion 31 has a base end formed in a shape of a thread groove and a tip end having a larger diameter than the base end side. As a result, a step groove portion 32 is formed between the tip end side and the base end side.

In one embodiment, a liquid soaking holder 30 of FIG. 5 can comprise the following: an outer tube portion 33 fitted and fixed into an opening portion 31 in a storage tank 29, an inner tube portion 34 inserted through a hollow portion in an outer tube portion 33 and extending from an inside to an outside of the storage tank 29, and the core 35 fixed in a hollow portion of the inner tube portion 34. Through capillary action, the core 35 soaks up the spray liquid in the storage tank 29. The outer tube portion 33 and the inner tube portion 34 of the liquid soaking holder 30 are connected by a connecting bridge 36. Surplus spray liquid, soaked up by the core 35, returns into the storage tank 29 from a portion between the tube portions 33 and 34 that are not connected by the connecting bridge 36. The connecting bridge 36 maintains an equal internal pressure and external pressure of the storage tank 29. This prevents the spray liquid in the storage tank 29 from spouting as the internal pressure increases due to increase in air temperature. The inner tube portion 34, extending outside the storage tank 29, forms a tip end side to cover a tip end side of the core 35 protruding from the storage tank 29. An opening window 38 is formed in the tip end side of the inner tube portion 34 so that only a front side of a tip end portion 37 of the core 35 is exposed. A seal body 39 is fixed to the outer tube portion 33 so as to surround an outer periphery of the outer tube portion 33.

In another embodiment, a cap (not shown), such as a screw cap, can be fitted into the step groove portion 32 formed at the opening portion 31 of the storage tank 29, thus preventing evaporation of the spray liquid from the storage tank 29.

The core 35 may be a cylindrical shape. Preferably, the core 35 is formed from a material that liquid can flow through, particularly without assistance and in opposition to gravity, such as by capillary action. The material for core 35, may be felt, nonwoven fabric made of natural pulp, and material obtained by twining fibers such as polypropylene and polyethylene may be used. In a preferred embodiment, the core is a 0.240 g/cc wick, made of HRM that is 120 mm length with a 0.7 mm diameter.

Next, according to another embodiment of the invention, a method of assembling the liquid sprayer 1 is described. According to this embodiment, first, the power supply unit 7 is housed into box 25 of support member 3. The connecting shafts 49 of the support arm 44 are fitted into the connecting holes 16 formed in the opposite support plates 15 of the lid member 2 to support the support arm 44 between the opposite side faces of the lid member 2. Next, the opposite fitting shafts 14 of the lid member 2 are inserted into the opposite fitting holes 24 in the support member 3 to connect the lid member 2 to the support member 3 so that the lid member 2 can turn. After that, an electric wire (not shown) extending from the power supply unit 7 is connected to the transducer 46 of the transducer unit 6. Then, the spray liquid storage unit 5 is formed by inserting the liquid soaking holder 30 into the opening portion 31 of the storage tank 29 that is disposed on the support shelf 26 of the support member 3 and the step groove portion 32 of the spray liquid storage unit 5 is fitted into the back holding plate 41. Lastly, the lid member 2 is closed onto the support member 3 and the lock pins 28 of the support member 3 are fitted into the lock holes 19 in the lid member 2 to thereby lock opening and closing of the lid member 2 with respect to the support member 3. At this time, the front holding plate 43 of the lid member 2 is fitted into the step groove portion 32 of the spray liquid storage unit 5 and the spray liquid storage unit 5 is fixed while sandwiched between the front and back holding plates 43 and 41.

In the assembled liquid sprayer 1, the transducer 46 and the core 35, that the transducer 46 is in contact, are exposed through the spray hole 8 in the lid member 2. When the electric power is supplied from the power supply unit 7 to vibrate the transducer 46, the spray liquid retained by the core 35 is turned into the mist by the vibration of the transducer 46 and sprayed outside the case main body 4 through the spray hole 8 in a direction generally forward and upward. Because the tip end portion 37 of the core 35 is in contact with the transducer 46 and the front side of the tip end portion 37 is exposed through the opening window 38 covered with the liquid soaking holder 30, the mist is prevented from being sprayed inside the case main body 4 and the spray liquid is prevented from wastefully evaporating from the core 35. As it will be understood by those skilled in the art, the transducer 46 contacts the core 35 with enough distance such that the vibration of the transducer 46 draws liquid through the mesh to dissipate the spray liquid as a mist, but not so close that the core 35 restricts movement of the transducer 46.

In a preferred embodiment, the spray mist sprayed outside the main body through the spray hole is projected outside the main body in a substantially horizontal direction. In another preferred embodiment, the spray mist comprises droplets from about 1 μm to 10 μm, and more preferably droplets of less than 7 μm.

To replace the spray liquid storage unit 5, insert a pin (not shown) into the lock hole 19 in the lid member 2 to push the lock pins 28 inward. The locking of the lid member 2 to the support member 3 is released and the lid member 2 is turned upward with respect to the support member 3. Next, the old spray liquid storage unit 5 is detached from the support shelf 26 and a new spray liquid storage unit 5 is fixed to the holding plate 41. Lastly, the lid member 2 is closed onto the support member 3 and locked.

Next, a positional relationship between the support arm 44 and the core 35 when the lid member 2 is opened and closed with respect to the support member 3 of the liquid sprayer 1, will be described based on FIGS. 6A to 6C. In each of FIGS. 6A to 6C, a lower portion of the case main body 4, the box 25, and the power supply unit 7 are not shown and an enlarged view showing a relationship between the connecting shaft 51 of the support arm 44 and the connecting hole 16 of the support plates 15 is shown.

First, if the lid member 2 is completely closed onto the support member 3, the spray liquid storage unit 5 is fixed in the case main body 4 sandwiched in between the front and back holding plates 43 and 41. As shown in FIG. 6A, a back face of the transducer 46 comes into contact with an edge portion 52 of a front side of the tip end portion 37 of the core 35. The core 35 is exposed from the opening window 38 of the liquid soaking holder 30 and a front face of the transducer 46 faces the spray hole 8 while oriented forward and upward. At this time, the restricting shafts 51 of the connecting shafts 49 are not interfering with the fan-shaped holes 18 of the connecting holes 16 and therefore the support arm 44 can turn in a front-back direction with respect to the support plates 15. Furthermore, because the lateral bar portion 45 and the transducer 46 are positioned on the front side of the axis of turning of the support arm 44, the center of gravity of the support arm 44 is positioned on the back side of the axis of turning and a force for turning backward is always acting on the support arm 44. Therefore, the weight of transducer unit 6, presses the transducer 46 in contact with and against the edge portion 52 of the front side of the tip end portion 37 of the core 35.

Next, if the lid member 2 is completely opened from the support member 3, as shown in FIG. 6B, the back face of the transducer 46 is separated from the edge portion 52 of the front side of the tip end portion 37 of the core 35. At this time, the restricting shafts 51 of the connecting shafts 49 are interfering with the fan-shaped holes 18 of the connecting holes 16. As a result, the backward turning of the support arm 44 is restricted and the support arm 44 is lifted together with the lid member 2.

Figure 6A:
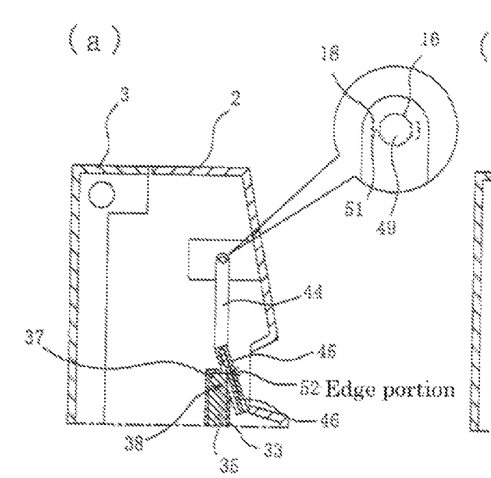
Figure 6B:
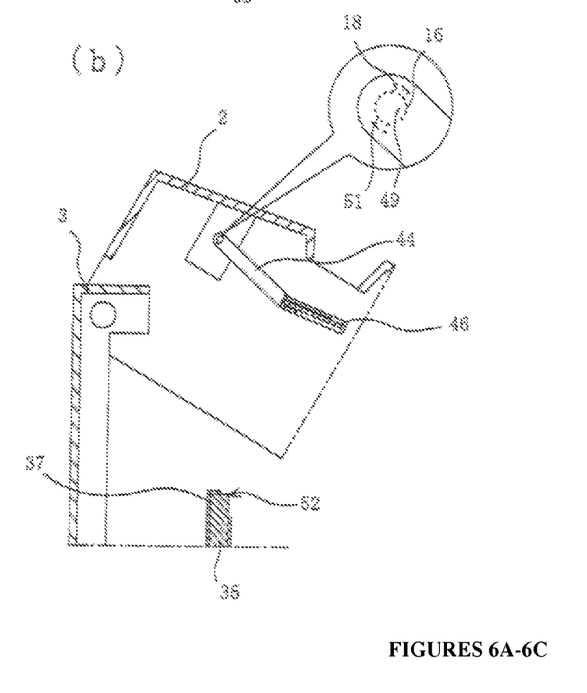
Figure 6C:
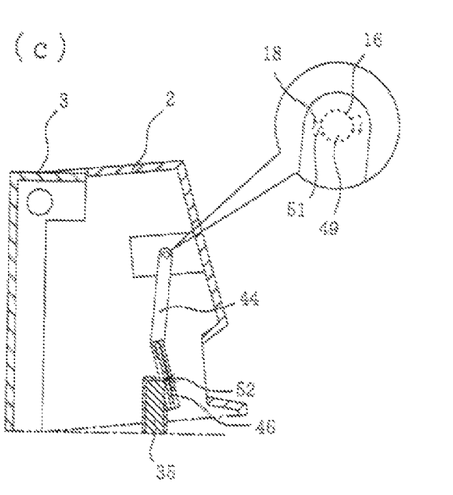
Figure 7:
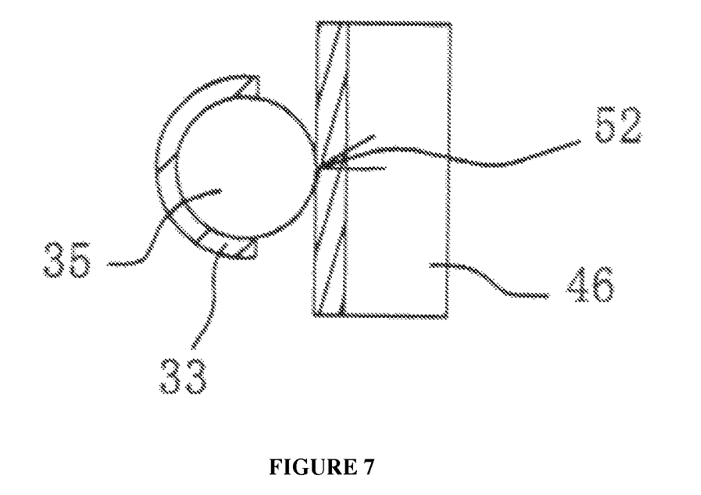
Figure 8A:
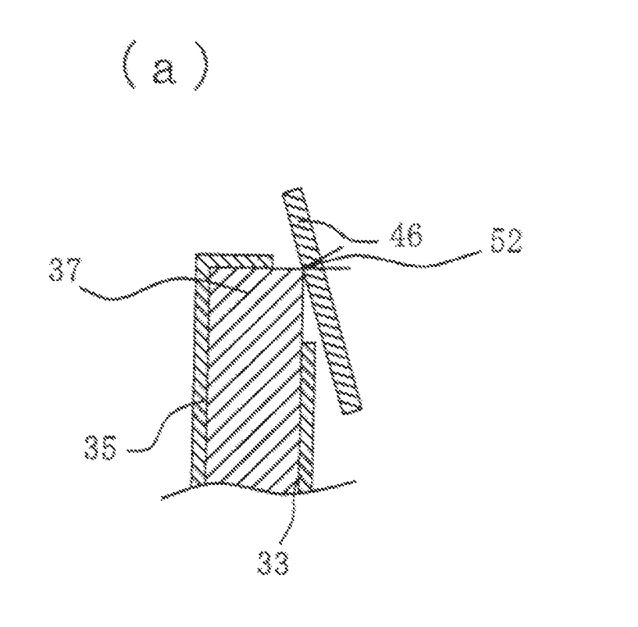
Figure 8B:
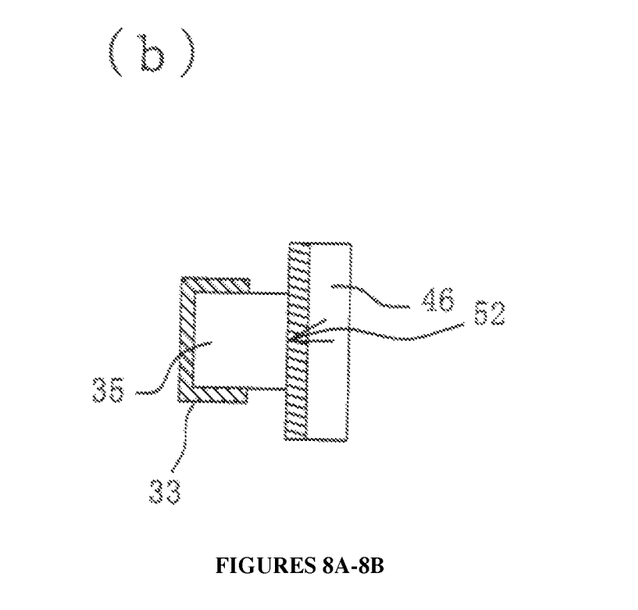

Then, if the lid member 2 is partly closed onto the support member 3, as shown in FIG. 6C, a lower end of the back face of the transducer 46, fixed to the support arm 44, comes into contact with the edge portion 52 of the front side of the tip end portion 37 of the core 35. At this time, the restricting shafts 51 of the connecting shafts 49 are not interfering with the fan-shaped holes 18 of the connecting holes 16 and, as a result, the support arm 44 can turn in the front-back direction with respect to the support plates 15. Moreover, because the lateral bar portion 45 and the transducer 46 are positioned on the front side of the axis of turning of the support arm 44, the center of gravity of the support arm 44 is positioned on the back side of the axis of turning and the force for turning backward is always acting on the support arm 44.

Figure 5:
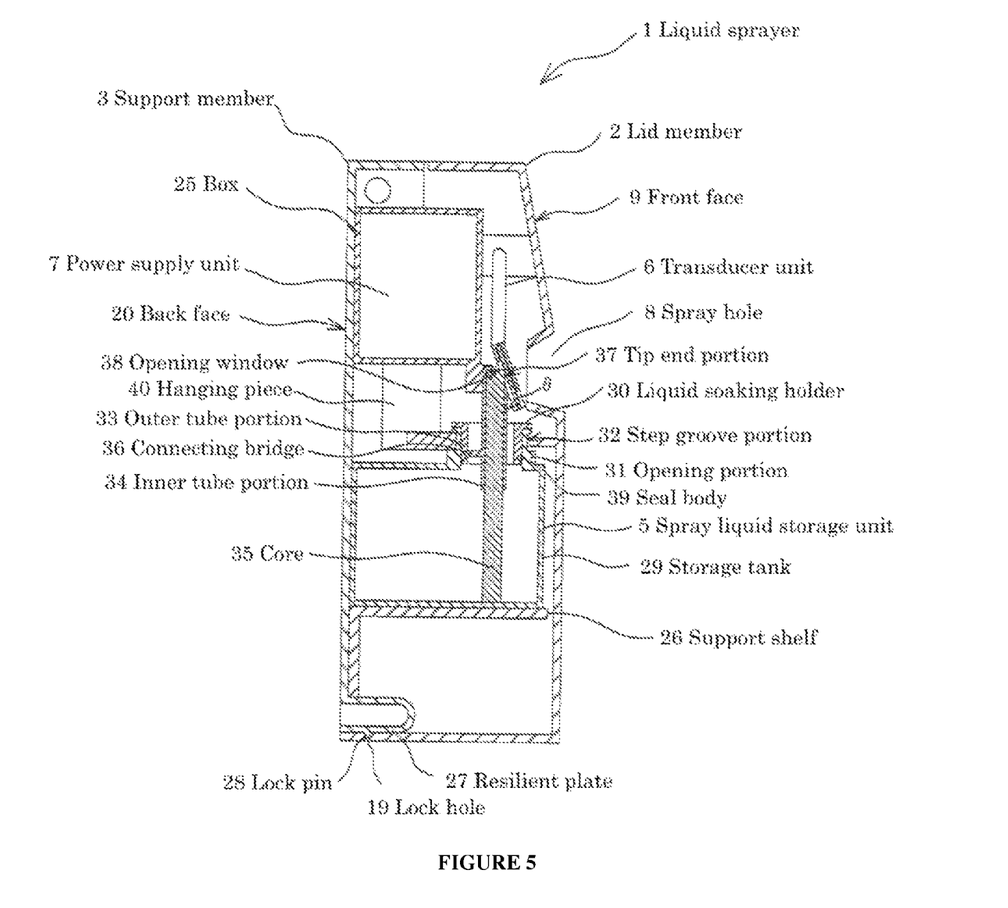

If the lid member 2 is completely closed onto the support member 3, they come into the state shown in FIG. 6A again An inclination angle θ, as seen in FIG. 5, is preferably 10° to 45° and more preferably 10° to 30° between the front face of the transducer 46 and the flat front face of the core 35. The inclination angle θ is oriented toward the spray hole 8 when the back face of the transducer 46 is in contact with the tip end portion 37 of the core 35. If the inclination angle is larger than 45°, a horizontal dispersion distance of the spray liquid turned into the mist is short. If the inclination angle is smaller than 10°, the vertical dispersion distance of the spray liquid turned into the mist is short. A short vertical or horizontal dispersion of the mist makes it impossible for wide dispersion of the mist. Moreover, if inclination angle is smaller than 10°, a large amount of spray liquid accumulates in the clearance formed between the transducer and the core 35 and evaporation of the spray liquid during stoppage increases thereby shortening the life of the storage tank.

The spray hole 8 of the lid member 2 opens in a portion of the lid member 2. The spray hole 8 faces and extends towards the front face of the transducer 46 via a tubular passage. In this way, the spray liquid turned into the mist by the transducer 46 is properly dispersed to the outside of the case main body 4.

According to one embodiment, the core 35 has a peripheral round shaped face and the transducer 46 is pressed under the weight of the transducer unit 6, due to turning the support arm 44 to contact the front side of the tip end portion of the core. Therefore, it is possible to easily and properly bring the back face of the transducer 46 and the tip end portion of the core 35 into contact with each other.

Another embodiment of the present invention is shown in FIGS. 8A and 8B. This embodiment is a variation of the core described above and the same reference numerals as those in FIGS. 1 to 6C designate the same or corresponding portions in FIGS. 8A and 8B. FIGS. 8A and 8B show a positional relationship between a core and a transducer when a support member is closed with respect to a lid member, wherein FIG. 8A is a vertical sectional view and FIG. 8B is an end view of the core and the transducer shown in FIG. 8A cut in a horizontal direction in a position where they are in contact with each other.

The core 35 in the above described embodiment is formed in a shape of a square prism as shown in FIG. 8B. Any one of the faces of the core 35 extending in the vertical direction is positioned to face a spray hole 8. When the lid member 2 is closed onto the support member 3, a back face of the transducer 46 comes in contact with an edge portion 52. The edge portion is formed by a front face and an upper face positioned on a front side of a tip end portion 37 of the core 35, exposed from the opening window 38.

In the above described embodiment, a contact face between the transducer and the core is larger increasing the efficiency of turning spray liquid into mist as compared to the first embodiment described above that has a cylindrical core.

The shape of the core in the invention is not limited to those shown in the above-described respective embodiments. It is essential only that the shape of the core has the edge portion that can come in contact with the back face of the transducer on the front side of the tip end portion facing the spray hole. The shape other than the front side of the tip end portion is not limited, as long as the core can soak up the spray liquid.

The spray liquid in the invention may be fragrance, deodorant, germicide, or the like but is not limited to them. The spray liquid may be other agents that can be turned into mist by the ultrasonic vibration of the transducer.

Although the center of gravity of the support arm is positioned on the back side of the axis of turning so that the force for turning backward acts on the support arm when the transducer fixed to the support arm is brought into close contact with and pressed against the core in the method employed in First Embodiment described above, the method is not limited to it. For example, resilient bodies such as springs may be disposed at connecting portions between the support arm and the support plates to thereby always press the support arm backward.

Although the present invention has been described with a degree of particularity, it is understood that the present disclosure has been made by way of example and that other versions are possible. As various changes could be made in the above description without departing from the scope of the invention, it is intended that all matter contained in the above description or shown in the accompanying drawings shall be illustrative and not used in a limiting sense. The spirit and scope of the appended claims should not be limited to the description of the preferred versions contained in this disclosure.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. §112.

DESCRIPTION OF REFERENCE SIGNS

1 Liquid sprayer
2 Lid member
3 Support member
4 Case main body
5 Spray liquid storage unit
6 Transducer unit
7 Power supply unit
8 Spray hole
9 Front face
10 Left side face 11 Right side face
12 Upper face
13 Lower face
14 Fitting shaft
15 Support plate
16 Connecting hole
17 Circular hole
18 Fan-shaped hole
19 Lock hole
20 Back face
21 Left side face
22 Right side face
23 Upper face
24 Fitting hole
25 Box
26 Support shelf
27 Resilient plate
28 Lock pin
29 Storage tank
30 Liquid soaking holder
31 Opening portion
32 Step groove portion
33 Outer tube portion
34 Inner tube portion
35 Core
36 Connecting bridge
37 Tip end portion
38 Opening window
39 Seal body
40 Hanging piece
41 Back holding plate
42 Support piece
43 Front holding plate
44 Support arm
45 Lateral bar portion
46 Transducer
47 Protecting piece
48 Vertical bar portion
49 Connecting shaft
50 Round shaft
51 Restricting shaft
52 Edge portion

What is claimed is:

1. A liquid sprayer for dispensing a spray liquid comprising:
 a. a main body comprising:
  i. a support member having a back face, an upper portion, and a lower portion;
  ii. a power supply unit positioned on the upper portion of the support member;
  iii. a lid member having a front face, wherein the lid member is rotatably connected to the support member to an open position, that reveals the upper portion and lower portion of the support member, and a closed position; and
  iv. a spray hole formed on the front face of the lid member;
 b. a spray liquid storage unit that is supported by and positioned on a support shelf, the spray liquid storage unit comprising:
  i. a spray liquid housed in a storage tank; and
  ii. a core for soaking up the spray liquid, wherein the spray liquid storage unit is removable from the main body when the lid member is in the open position; and
 c. a transducer unit comprising a transducer disposed inside the lid member and electrically connected to the power supply unit, such that when the lid member is in the closed position, the transducer is in contact with a front face of a tip end portion of the core with a front face of the transducer oriented forward and upward; and the core, transducer and spray hole are substantially aligned horizontally, such that when electric power is supplied from the power supply unit to the transducer, the spray liquid retained in the core is turned into a spray mist by vibration of the transducer and sprayed outside the main body through the spray hole.

2. The liquid sprayer according to claim 1 wherein when the lid member is in the open position, the upper portion and lower portion of the support member are revealed, and wherein when the lid member is in the closed position, the transducer unit disposed in the lid member is disposed parallel to a front face of the core.

3. The liquid sprayer according to claim 1 wherein the lid member further comprises side faces rising from opposite sides of the front face of the lid member, and wherein a support arm is positioned between the opposite side faces of the lid member and the transducer is affixed to the support arm, that raises and lowers the transducer with the lid member and aligns the transducer with the spray hole and the core.

4. The liquid sprayer according to claim 1 wherein the core has a round peripheral face.

5. The liquid sprayer according to claim 1, wherein the front face of the tip end portion of the core extends in a vertical direction and forms an inclination angle with the transducer between 10° to 45°.

6. The liquid sprayer according to claim 1 wherein the support member further comprises one or more support members for supporting one or both of the power supply unit and the spray liquid storage unit.

7. The liquid sprayer according to claim 1 wherein the spray mist sprayed outside the main body through the spray hole is projected outside the main body in a substantially horizontal direction.

8. The liquid sprayer according to claim 1 wherein the spray mist comprises droplets from about 1 µm to 10 µm.

9. The liquid sprayer according to claim 1 wherein the spray mist comprises droplets of less than 7 µm.

10. The liquid sprayer according to claim 1 wherein the lid member further comprises a lock hole that restricts opening of the lid member.

11. The liquid sprayer according to claim 1 wherein the main body further comprises a key pad for setting automatic spray intervals for release of the spray mist.

12. The liquid sprayer according to claim 11 wherein the key pad is an electronic display.

13. The liquid sprayer according to claim 1 wherein the main body further comprises a power indicator display.

14. The liquid sprayer according to claim 1 wherein the main body further comprises a light sensor for automatic turn off or turn on of the liquid sprayer.

15. The liquid sprayer according to claim 1, wherein the spray liquid storage unit further comprises a cap for reducing evaporation of the spray liquid from the storage tank.

16. The liquid sprayer according to claim 1, wherein the core further comprises a base end portion, wherein the front face of the tip end portion of the core is in contact with the transducer, and the base end portion extends from the tip end portion into the storage tank.

17. The liquid sprayer according to claim 1, wherein the transducer is in contact with and pressed against the core.

18. The liquid sprayer according to claim 17, wherein the front face of the tip end portion of the core is in contact with the transducer, and the transducer is oriented forward and upward with respect to the core.

19. The liquid sprayer according to claim 17, wherein an edge portion of the front face of the tip end portion of the core is in contact with the transducer.

* * * * *